US008751961B2

(12) United States Patent
Bird et al.

(10) Patent No.: US 8,751,961 B2
(45) Date of Patent: Jun. 10, 2014

(54) SELECTION OF PRESETS FOR THE VISUALIZATION OF IMAGE DATA SETS

(75) Inventors: Ian Douglas Bird, Edinburgh (GB); Colin John Roberts, East Linton (GB)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/361,003

(22) Filed: Jan. 30, 2012

(65) Prior Publication Data

US 2013/0198687 A1    Aug. 1, 2013

(51) Int. Cl.
G06F 3/048    (2013.01)

(52) U.S. Cl.
USPC ......................................... 715/810

(58) Field of Classification Search
USPC ......................................... 715/810
See application file for complete search history.

(56) References Cited

U.S. PATENT DOCUMENTS

| | | | |
|---|---|---|---|
| 5,986,662 A | | 11/1999 | Argiro et al. |
| 6,658,080 B1 * | | 12/2003 | Poole et al. .................. 378/4 |
| 2005/0017972 A1 * | | 1/2005 | Poole et al. .................. 345/424 |
| 2008/0232718 A1 * | | 9/2008 | Avinash et al. ............... 382/305 |
| 2008/0267471 A1 * | | 10/2008 | Yu et al. ........................ 382/128 |
| 2012/0219197 A1 * | | 8/2012 | Piper et al. .................... 382/131 |

FOREIGN PATENT DOCUMENTS

JP    2006-61601    3/2006

* cited by examiner

*Primary Examiner* — William Bashore
*Assistant Examiner* — Rayeez Chowdhury
(74) *Attorney, Agent, or Firm* — Oblon, Spivak, McClelland, Maier & Neustadt, L.L.P.

(57) ABSTRACT

A computer-automated image visualization method for displaying images from an image data set comprising a plurality of image elements, each image element having an associated image value, including providing a visualization application with a library of presets, each preset defining a mapping between image values and their representation in a graphical user interface; loading an image data set from a data file containing the image data set; displaying an initial representation of the loaded image data set on a graphical user interface; receiving user input from a location in the representation to indicate a region of interest in the image data set; determining properties of image elements in the region of interest; making a list of potentially suitable presets from the library of presets based on the determined properties of the region of interest; and presenting the potentially suitable presets to the user for selection.

18 Claims, 13 Drawing Sheets

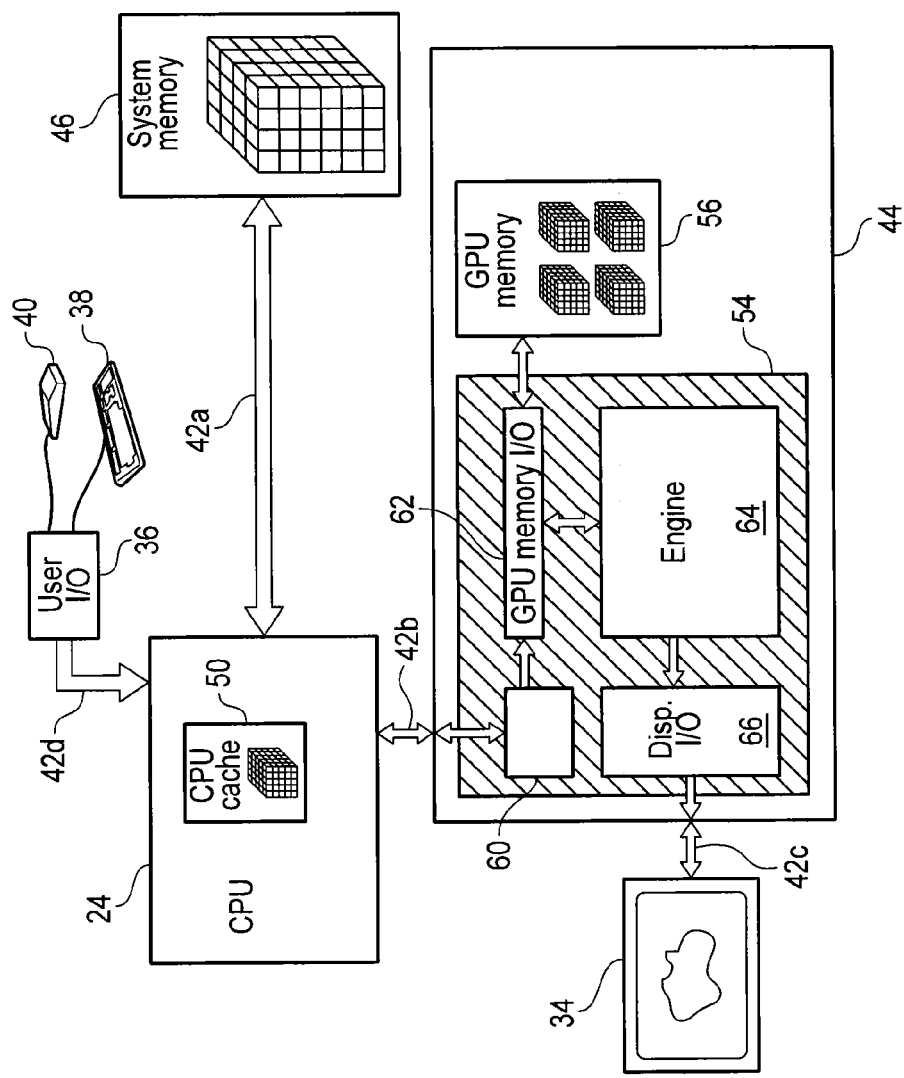
F I G. 5

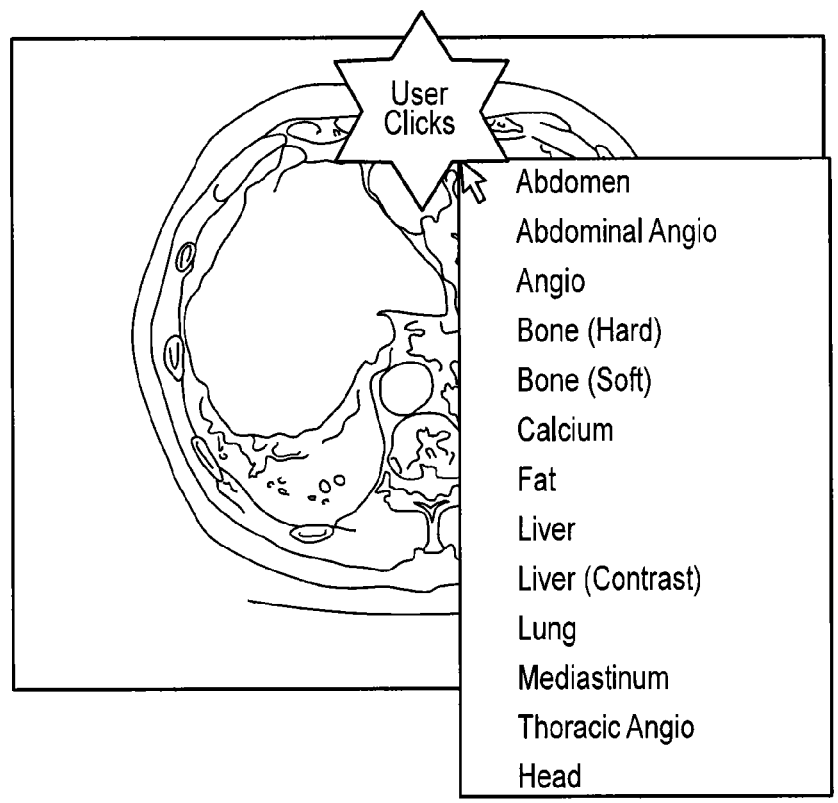
F I G. 11A
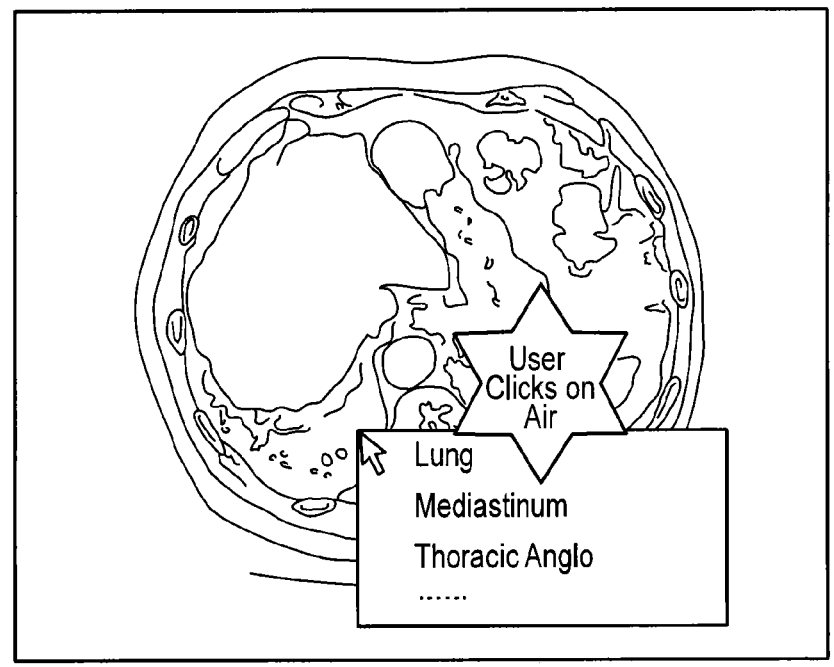
F I G. 11B

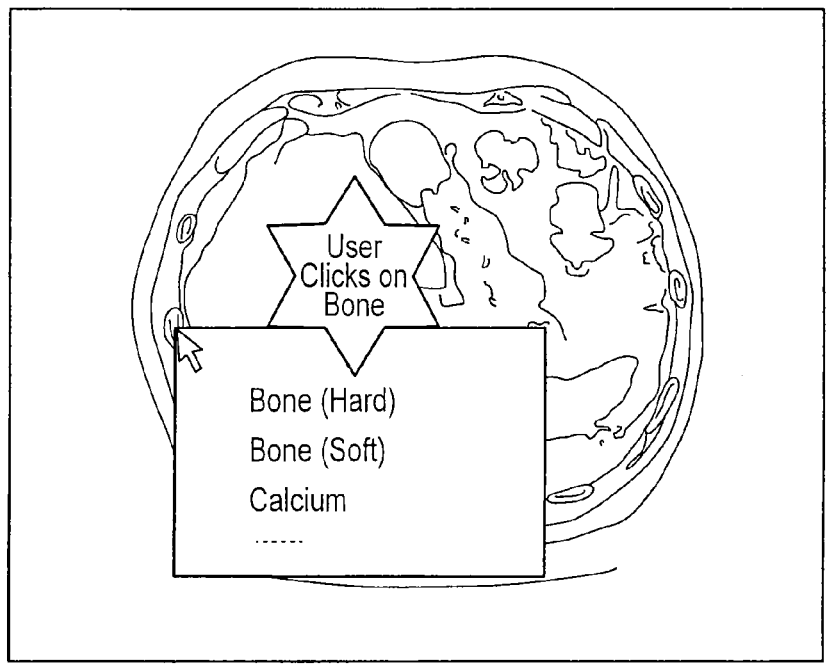
F I G. 11E
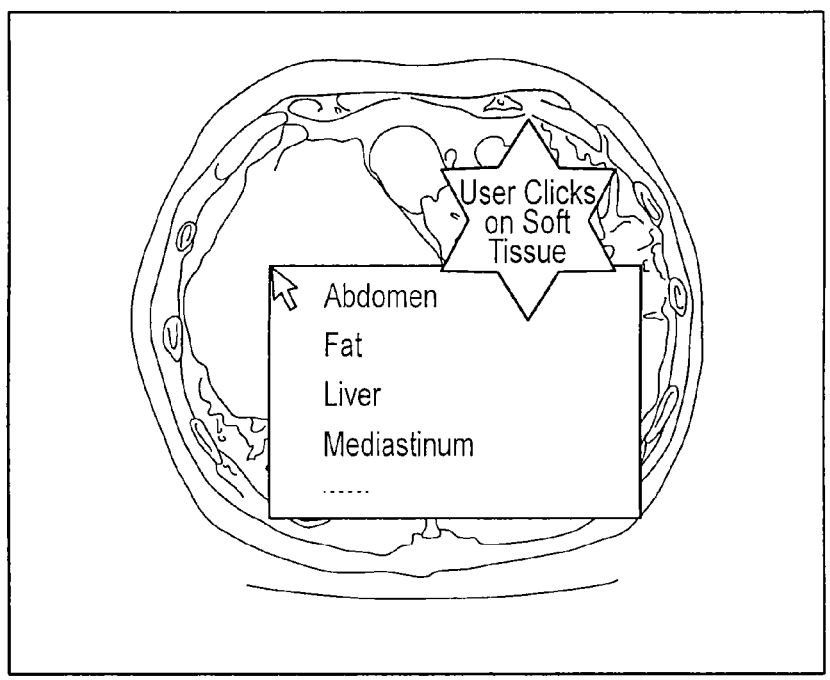
F I G. 11F

SELECTION OF PRESETS FOR THE VISUALIZATION OF IMAGE DATA SETS

BACKGROUND OF THE INVENTION

Embodiments described herein generally relate to the selection of presets for the visualization of image data sets.

In the medical field, two-dimensional (2D) and three-dimensional (3D) image data sets are collected by a variety of techniques—referred to as modalities in the field—including conventional X-ray, computer-assisted tomography (CT), magnetic resonance (MR), ultrasound and positron-emission-tomography (PET). Examples of 2D images include not only conventional X-ray images, but also 2D images derived from 3D image data sets, i.e. volume data sets, such as a "slice" of a CT scan or a "slab" of volume data from a CT scan in a multi-planar reformatting (MPR) view. Time resolved 3D studies are also well known and are usually referred to as 4D studies, with time being the fourth "dimension". For example, time-resolved perfusion in abdominal organs is measured using 4D dynamic contrast enhanced CT (DCE-CT). It is also known to co-present images of the same patient taken with different modalities, such as combining CT and PET scans into a single image. These combined representations are sometimes referred to as 5D studies.

In a visualization application, images presented to the user are represented by a gray scale, there being one gray scale in a monochrome representation and multiple gray scales in color representations. For the sake of simplicity of explanation, we assume monochrome representation in the following. The gray scale values map back to the scanner's originally sampled image value (e.g. in Hounsfield Units (HUs)). It is a known fact that human vision cannot distinguish very well between different shades of gray. It has been said that a person can, at most, only perceive about 20-30 different levels of gray at a time. Therefore, it is often helpful to confine the gray scale to a relatively small range of signal values which contains the tissue type of interest, rather than attempting to visualize the full scale at once. The restricted range of the gray scale is conventionally defined in terms of a "window width" and a "window level". The window level defines the center point within the range of signal values to be displayed. The window width is the range of densities around this center point to be displayed as a gray scale value from white to black. In a monochrome representation, densities which fall below this range will be displayed as black, and densities above this scale will be displayed as white. For example, in a CT data set, bone is known to be dense and hence have high values of Hounsfield Unit (HU). To provide a good visualization of bone features in a CT data set, the window level is therefore set to a high value, e.g. 350. The window width is set to be relatively large, since bone tissue is known to span a large range of HUs, e.g. 1200.

A particular combination of window level and window width known to be suitable for visualizing particular tissue types or other features is referred to in the field as a "preset". A preset thus defines a mapping between image values in an image data set and what shade pixels or voxels having those image values are given when displayed to a user. For any given modality, a variety of presets will be stored and available for user selection. For example, if the user has a CT data set loaded, the user can switch between different presets suitable for showing different organs, blood vessels, bone and so forth. While the term preset probably originated because of the fact that window settings were pre-determined and stored for user selection, somewhat confusingly the term preset is now used more generally in the field to refer to any set of visualization parameters, even if the set is not pre-determined. For example, some applications adjust or set window settings on-the-fly during a user viewing session. The term preset in this document is used in this industry standard way to include both pre-determined and on-the-fly-determined visualization parameters.

Over time, within any given modality a wide variety of clinical uses has developed. For example, CT scanning may be used to study bone and various types of tissue from relatively hard to relatively soft. In CT, the values of the voxels contained in the volume data set can span a very wide range. Consequently large numbers of presets have been found, each optimized for particular clinical uses. Moreover, many CT and MR studies use contrast agents to highlight features of clinical interest. There are many different types of contrast agent with different properties for the relevant modality. For example, there may be a preset optimized for viewing angiograms taken with a particular contrast agent. These clinical application specific, pre-optimized visualization parameters are typically stored and made available to users as elements in a library of presets with clinically relevant names to assist a user making an appropriate selection of preset. Users can also make their own presets and store them in the library, either ab initio or by modifying existing presets.

An example list of presets for 2D X-ray images or MPR views of volume data sets acquired by CT might be:
1) Abdomen
2) Abdominal Angio
3) Angio
4) Bone (Hard)
5) Bone (Soft)
6) Calcium
7) Fat
8) Liver
9) Liver (Contrast)
10) Lung
11) Mediastinum
12) Thoracic Angio
13) Head As clinical knowledge becomes ever more developed and specialized, more and more presets are defined and stored, and as a result it becomes ever more difficult for a user to make the most appropriate choice of preset from the large number available. For example, the choice of preset will depend on the subject, what type of data is being represented, whether (and if so, how) the data are calibrated and what particular features of the image data set the user might wish to highlight, which will depend on the clinical application.

BRIEF DESCRIPTION OF THE DRAWINGS

Embodiments of the Invention are now described by way of example only with reference to the following drawings.

FIG. 5 schematically shows some of the features of the computer of FIG. 4 in more detail.

FIG. 10b is the same as FIG. 10a except that the field of view has been zoomed in.

FIG. 11a is a first example screen shot from a GUI presenting a 2D image which is a horizontal section of a patient's abdomen where the underlying data is conventional 2D X-ray data obtained from a CT scan together with a dropdown list of presets available for user selection.

FIGS. 11b-11g are further example screen shots of the same image section as FIG. 11a where the dropdown list of presets presented on the GUI for user selection has adaptively responded to the user pointing and clicking on different locations on the 2D image.

DETAILED DESCRIPTION

Figure 1:
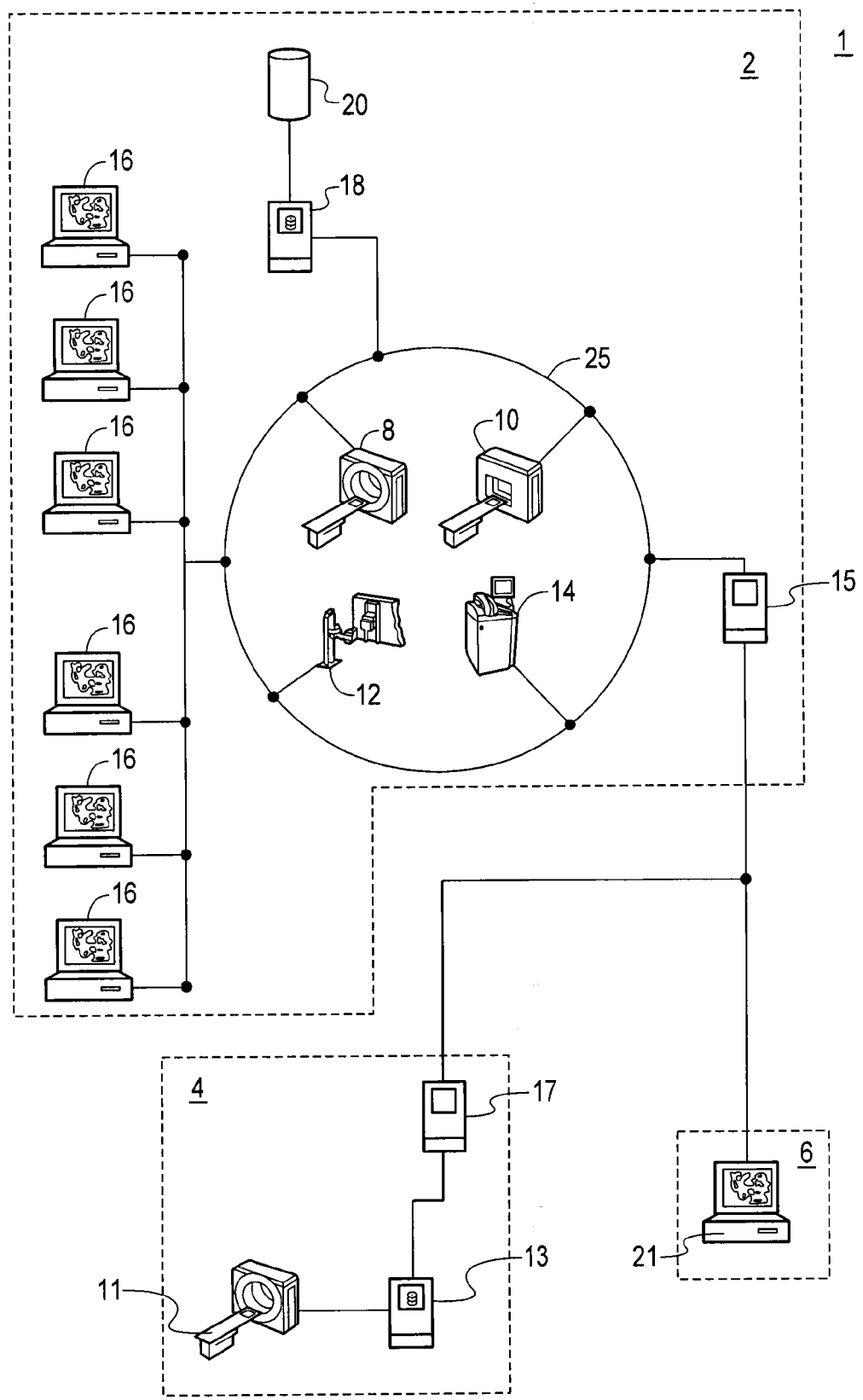
FIG. 1 is a schematic diagram showing an exemplary network of diagnostic devices and associated equipment.

Certain embodiments of the invention provide a computer-automated image visualization method for displaying images from an image data set comprising a plurality of image elements, each image element having an associated image value, the method comprising:
a) providing a visualization application with a library of presets, each preset defining a mapping between image values and their representation in a graphical user interface;
b) loading an image data set from a data file containing the image data set;
c) displaying an initial representation of the loaded image data set on a graphical user interface;
d) receiving user input from a location in the representation to indicate a region of interest in the image data set;
e) determining properties of image elements in the region of interest;
f) making a list of potentially suitable presets from the library of presets based on the determined properties of the region of interest; and
g) presenting the potentially suitable presets to the user for selection.

The method may further comprise: making the list based also on header information stored in the data file. The header information used in making the list is selected from the group including:
a) modality information (e.g. CT, combined CT+SPECT);
b) contrast agent information (e.g. radiocontrast agent in a CT scan, hyperpolarized He or Xe in a lung MRI scan, Gd or iron oxide contrast agent in MRI);
c) anatomical information defining the Imaged body portion (e.g. foot, abdomen, head);
d) medical information specific to the diagnostic purpose of the Image data set (e.g. polyp analysis by virtual colonoscopy, or coronary angiogram);
e) medical information specific to the clinical position of the user (e.g. cardiac specialist, orthopedic surgeon).

The method may further comprise: making the list based also on segmentation data providing anatomical information about the region of interest.

The list may comprise a subset of the presets contained in the library.

The list may be sorted or otherwise presented having regard to potential suitability. Presentation of potential suitability can be achieved in a variety of ways. An example is presenting a list in which those presets determined to be most suitable are listed first. Another example would be to present those presets determined to be most suitable in a more prominent font.

It is possible to carry out the method with sorting and no filtering, or with filtering and no sorting. However, it is most preferred to combine filtering with sorting, where filtering is used to select a subset of potentially suitable presets from the library and sorting is used to sort among the filtered presets. For example, the sorting when used as a secondary criteria may be based on previous selections. It may sort according to how many times a particular preset has been selected by the individual user or how many times a particular preset has been selected by any user for visualizing the type of study that is loaded. Many other options for sorting are also possible.

The list may comprise a subset of the presets contained in the library sorted according to potential suitability with presets determined to be most suitable listed first.

The potentially suitable presets may be presented on the graphical user interface adjacent to the location where the user input is received. This feature means that a user's view is not diverted to a peripheral part of the graphical user interface in order to make a preset selection, or to a new window that pops up and overlays the representation. Rather, the user is able to select a preset while retaining his or her view in the general direction of the region of interest. This contributes considerably to the quality of the user experience.

The method may further comprise: storing the list of potentially suitable presets, for example in header information of the data file or in a log stored otherwise.

The method may further comprise: receiving the user selection from among the potentially suitable presets; and displaying a representation of the image data set using the selected preset.

If the list consists solely of one potentially suitable preset, the method may proceed directly to display a representation of the volume data set using that preset instead of presenting the list of potentially suitable presets to the user for selection, i.e. instead of step g) above.

The method may further comprise: storing the user selected preset in header information of the data file.

Certain embodiments relate to volume data sets, i.e. 3D data sets in which case the image data set is a volume data set having voxels as its image elements, and wherein each voxel has an associated voxel value as its associated image value.

The volume of interest could include a group of voxels defined by proximity to a point identified by the user input.

For 2D image data sets, the region of interest includes a group of pixels defined by proximity to a point identified by the user input.

The volume of interest could include a group of voxels or pixels defined by a segmentation seeded from a point identified by the user input. Alternatively, a simple approach would be to include all voxels within a sphere of a certain size from the point identified by the user input.

The properties of voxels used for the determination may be selected from the group including: a) voxel value, and b) statistical fluctuation in voxel value in said group of voxels.

For 3D X-ray images, voxel value is a parameter of X-ray stopping power/attenuation coefficient in Hounsfield Units.

Certain embodiments of the invention provide a computer program product, which may be a non-transitory computer program product, bearing machine readable instructions for carrying out the method.

Certain embodiments of the invention provide a computer system loaded with and operable to execute machine readable instructions for carrying out the method, the computer system comprising: a first memory unit, such as system memory, storing a data file containing an image data set; a second memory unit, such as system memory or central processor unit (CPU) memory, storing a visualization application with a library of presets, each preset defining a mapping between image values and their representation in a graphical user interface; an image processing unit, such as a graphics processor unit (GPU), operable to load an image data set from the data file; a display unit operable to display an initial representation of the loaded image data set on a graphical user interface; a user input device, such as a user input/output circuit in combination with the output of a touch screen, or to a mouse, keyboard or other peripheral device, operable to receive user input from a location in the representation to indicate a region of interest in the image data set; the image processing unit being further operable to: (i) determine properties of image elements in the region of interest; (ii) make a list of potentially suitable presets from the library of presets based on the determined properties of the region of interest; and (iii) present the potentially suitable presets to the user for selection on the display unit.

Certain embodiments of the invention provide an image acquisition device loaded with and operable to execute machine readable instructions for carrying out the method.

Embodiments of the present invention will be described hereinafter and in the context of a computer-implemented system, method and computer program product which may be stored on a non-transitory medium. Although some of the present embodiments are described in terms of a computer program product that causes a computer, for example a personal computer or other form of workstation, to provide the functionality required of some embodiments of the invention, it will be appreciated from the following description that this relates to only one example of some embodiments of the present invention. For example, in some embodiments of the invention, a network of computers, rather than a stand-alone computer, may implement the embodiments of the invention. Alternatively, or in addition, at least some of the functionality of the invention may be implemented by means of special purpose hardware, for example in the form of special purpose integrated circuits (e.g., Application Specific Integrated Circuits (ASICs)).

FIG. 1 is a schematic representation of an exemplary network 1 of computer controlled diagnostic devices, stand-alone computer workstations and associated equipment. The network 1 comprises three components. There is a main hospital component 2, a remote diagnostic device component 4 and a remote single user component 6. The main hospital component 2 comprises a plurality of diagnostic devices for acquiring patient images, in this example, a CT scanner 8, a MR imager 10, a digital radiography (DR) device 12 and a computed radiography (CR) device 14, a plurality of computer workstations 16, a common format file server 18, a file archive 20 and an internet gateway 15. All of these features are inter-connected by a local area network (LAN) 25.

The remote diagnostic device component 4 comprises a CT scanner 11, a common format file server 13 and an Internet gateway 17. The CT scanner 11 and file server 13 are commonly connected to the internet gateway 17, which in turn is connected via the internet to the Internet gateway 15 within the main hospital component 2.

The remote single user component 6 comprises a computer workstation 21 with an internal modem (not shown). The computer workstation 21 is also connected via the internet to the Internet gateway 15 within the main hospital component 2.

The network 1 is configured to transmit data within a standardized common format. For example, the CT scanner 8 initially generates a source data set, i.e. a 3D image data set, from which an operator may derive an appropriate 2D image. The 2D image is encoded in a standard image data format and transferred over the LAN 25 to the file server 18 for storage on the file archive 20. A user working on one of the computer workstations 16 may subsequently request the image, the file server 18 will retrieve it from the archive 20 and pass it to the user via the LAN 25. Similarly, a user working remotely from the main hospital component 2, either within the remote diagnostic device component 4, or the remote single user component 6, may also access and transmit data stored on the archive 20, or elsewhere on the network 1.

The software operating on or from the computer workstations 16, 21 is configured to conform to the common image data format. The standardization of the image data format ensures that different software applications on the computers 16, 21, the file servers 13, 18 and file archive 20 and the output from the different computer controlled diagnostic devices 8, 10, 11, 12, 14 can share image data.

The most common image data format currently employed for medical applications is the "Digital Imaging and Communications in Medicine" format, usually referred to as DICOM. The DICOM standard is published by the National Electrical Manufacturers' Association of America.

Figure 2:
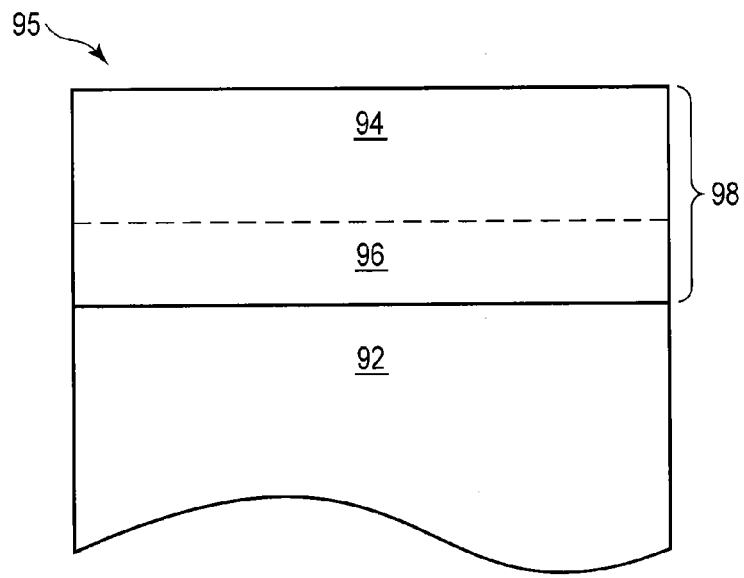
FIG. 2 is a schematic diagram representing the internal structure of a file which conforms to the DICOM standard.

FIG. 2 is a schematic representation of a computer file 95 which is conformant to the DICOM standard. The computer file 95 contains a header portion 98 and an image data portion 92. The header portion 98 is divided into a first header portion 94 and a second header portion 96. The DICOM standard provides the image data portion 92 for storage of the data comprising an image in a standard image data format, and the header portion 98 for storage of ancillary data associated with the image. The first header portion 94 is provided for storage of details which are commonly used and explicitly specified in the DICOM standard. These details are divided into modules such as; patient module, visit module, study module, results module, interpretation module, common composite image module, modality specific module. Within these modules, the inclusion of individual details may be mandatory, conditional or optional. The second header portion 96 is provided for storage of user specific information and comprises what are commonly called private tag information. These can be any details which a user would like to store with an image, but which are not specifically provided for by the DICOM standard for inclusion in the first header portion 94. A typical maximum size for the header portion 98 is 16 kilobytes and this limits the volume of information which may be stored there.

The diagnostic devices, file servers, file archives and computers are all designed to communicate by the transfer of DICOM format files.

The header information may contain data relating to the acquisition, such as patient information, what if any contrast agent was used, as well as information on the diagnostic device including its modality, dose and so forth. These data are often referred to as metadata. The header may also be used to store operational state data relating to the specific manipulation processes employed in deriving a particular 2D representation from an original 3D or 4D data set. Moreover, the header may be used to store notes, such as instructional information for technicians, further Illustrative images and clinical reports of the physician's findings. In some cases the totality of additional information to be associated with a DICOM file is too large for storage in the header of the DICOM file(s) containing the volume data set(s) in which case one or more additional DICOM files are used to store this data. The additional DICOM files are associated with the DICOM files containing the volume data set, and the additional information may be stored not only in the header portion of such additional DICOM files but also the image portion. An Individual study may comprise multiple DICOM files which are grouped or associated to allow for their common storage and retrieval.

There is a large range of data that may be recorded together with the image volume data set. For example, details may be stored about some or all of the following:

1) Acquisition Modality
2) Whether contrast agent was used, and if yes what contrast agent.
3) State of graphical user interface elements that control parameters of visualization.
4) Medical volume or multi-frame image data.
5) Medical image data.
6) Medical signal data acquired over time.
7) The name, age, and other details that identify the patient.
8) Information that identifies the hospital, physician, type of procedure, and other details of the case.
9) Additional medical observations or measurements entered directly.
10) Information about the medical history of the patient.
11) Report information, comprising text, images, measurements, and references linking findings to particular locations in the patient.
12) Other readable information, for example instructions or comments from one medical professional to another.
13) Unique identifier of images or other data objects containing the original medical data.
14) Study number, series number, acquisition number, or other administrative data that identifies the original medical data.
15) File names, URLs, network server identifications, or related data that describes the location of the original medical data.
16) Volume rendering parameters such as opacity and color parameters.
17) Surface rendering parameters such as threshold parameters.
18) Tissue segmentation and/or selection information.
19) Number of frames, rendering type, and geometric and other properties of movie sequence.

Figure 3:
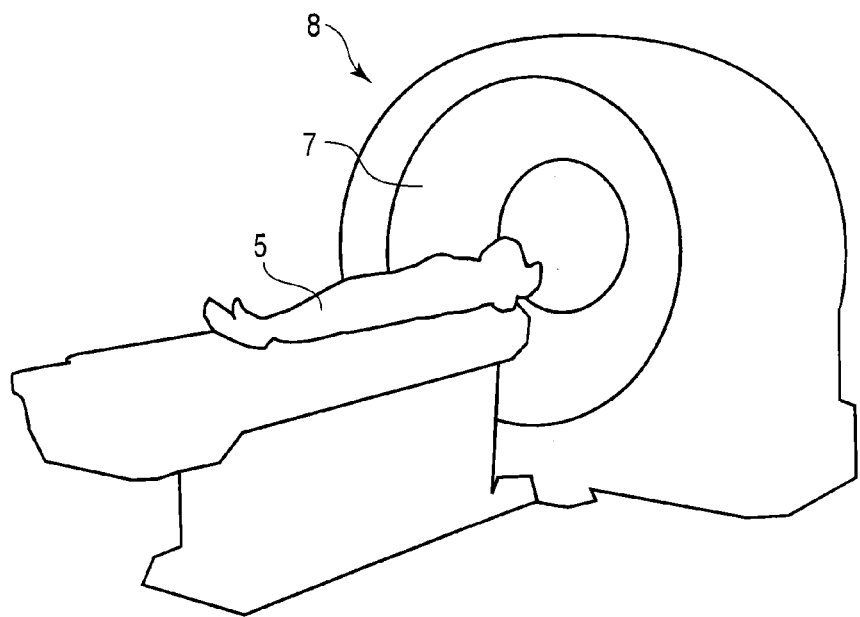
FIG. 3 shows a generic CT scanner for generating volume data.

FIG. 3 is a schematic perspective view of a generic scanner, most especially a computer-assisted tomography (CT) scanner 8, for obtaining a 3D X-ray scan of a region of a patient 5. A patient's abdomen including one or more organs or other anatomical features of interest is placed within a circular opening 7 of the scanner 8. A series of image slices through the patient's abdomen is taken. Raw image data are derived from the scanner and could comprise a collection of one thousand 2D 512×512 data subsets, for example. These data subsets, each representing a slice of the region of the patient being studied, are combined to produce volume data. The volume data, which makes up a 3D Image data set, comprise a collection of voxels each of which corresponds to a pixel in one of the slices. Thus the volume data are a 3D representation of the feature imaged and various user-selected 2D projections (output images) of the 3D representation can be displayed (typically on a computer monitor).

Different imaging modalities (e.g. CT, MR, PET, ultrasound) typically provide different image resolutions (i.e. voxel size), and the overall size of the volume imaged will further depend on the nature of the study. By way of concrete example, a volume data set may comprise an array of 512× 512×320 16-bit voxels arranged on a regular Cartesian grid defined by x-, y- and z-axes, with the voxels being spaced by 0.5 mm along each axis. This corresponds to an overall imaged volume of around 25 cm×25 cm×16 cm, which is adequate to encompass an abdominal organ of interest, such as a kidney, the liver, the bowel, the spleen or the pancreas. As is conventional, the volume data are aligned with transverse, sagittal and coronal planes. The xy-axes are in a transverse plane, the xz-axes are in a coronal plane and the yz-axes are in a sagittal plane.

Figure 4:
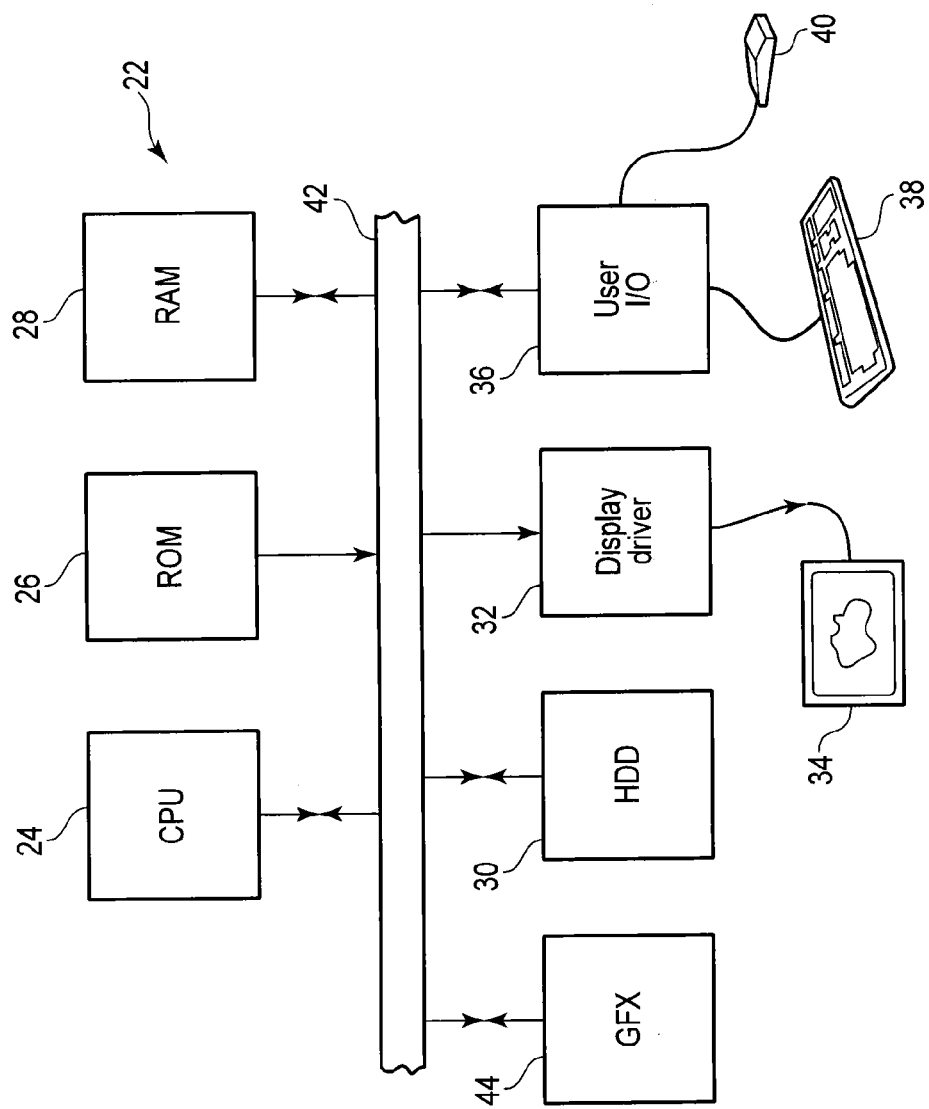
FIG. 4 schematically shows a computer for processing image data.

FIG. 4 schematically illustrates a general purpose computer system 22 configured to perform processing of volume data to generate two dimensional images. The computer 22 includes a central processing unit (CPU) 24, a read only memory (ROM) 26, a random access memory (RAM) 28, a hard disk drive 30, a display driver 32 and display 34 and a user input/output (IO) circuit 36 with a keyboard 38 and mouse 40. These devices are connected via a common bus 42. The computer 22 also includes a graphics card 44 connected via the common bus 42. The graphics card includes a graphics processing unit (GPU) and random access memory tightly coupled to the GPU (GPU memory).

The CPU 24 may execute program instructions stored within the ROM 26, the RAM 28 or the hard disk drive 30 to carry out processing of signal values associated with voxels of volume data that may be stored within the RAM 28 or the hard disk drive 30. The RAM 28 and hard disk drive 30 are collectively referred to as the system memory. The GPU may also execute program instructions to carry out processing of volume data passed to it from the CPU.

FIG. 5 schematically shows some of the features of the computer system shown in FIG. 4 in more detail. The RAM 28 and hard disk drive 30 are shown collectively as a system memory 46. Volume data obtained from the scanner 8 shown in FIG. 3 is stored in the system memory as shown schematically in the figure. To assist in showing the different data transfer routes between features of the computer system 22, the common bus 42 shown in FIG. 4 is schematically shown in FIG. 5 as a series of separate bus connections 42a-d. A first bus connection 42a connects between the system memory 46 and the CPU 24. A second bus connection 42b connects between the CPU 24 and the graphics card 44. A third bus connection 42c connects between the graphics card 44 and the display 34. A fourth bus connection 42d connects between the user I/O 36 and the CPU 24. The CPU includes a CPU cache 50. The graphics card 44 includes a GPU 54 and a GPU memory 56. The GPU 54 includes circuitry for providing an accelerated graphics processing interface 60, a GPU cache I/O controller 62, a processing engine 64 and a display I/O controller 66. The processing engine 64 is designed for optimized execution of the types of program instructions typically associated with processing 3D image data sets and carrying out 3D rendering of such data sets.

The user is able to select desired visualization parameters using the keyboard 38 and mouse 40 in combination with a graphical user interface (GUI) displayed on the display 34, for example using a movable screen icon in combination with a mouse, track pad etc. to point and click, a touch screen or other known techniques.

Methods described herein can be used within a hospital environment. In this case, the methods may usefully be integrated Into a stand-alone software application, or with a Picture Archiving and Communication System (PACS). A PACS is a hospital-based computerized network which can store volume data representing diagnostic images of different types in a digital format organized in a single central archive. For example, images may be stored in the DICOM format. Each image has associated patient information as described above. The archive is connected to a computer network provided with a number of workstations, so that users all around the hospital site can access and process patient data as needed. Additionally, users remote from the site may be permitted to access the archive over the Internet.

A user such as a radiologist, a consultant, or a researcher can access any image data set from the workstation, and generate and display movies or other images, such as a still images of a 2D or 3D data set or moving images from a 4D data set.

In the described embodiments, a computer implementation employing computer program code for storage on a data carrier or in memory can be used to control the operation of the CPU and GPU of the computer system. The computer program can be supplied on a suitable carrier medium, for example a storage medium such as solid state memory, magnetic, optical or magneto-optical disk or tape based media. Alternatively, it can be supplied on a transmission medium, for example a medium with a carrier such as a telephone, radio or optical channel.

Figure 6:
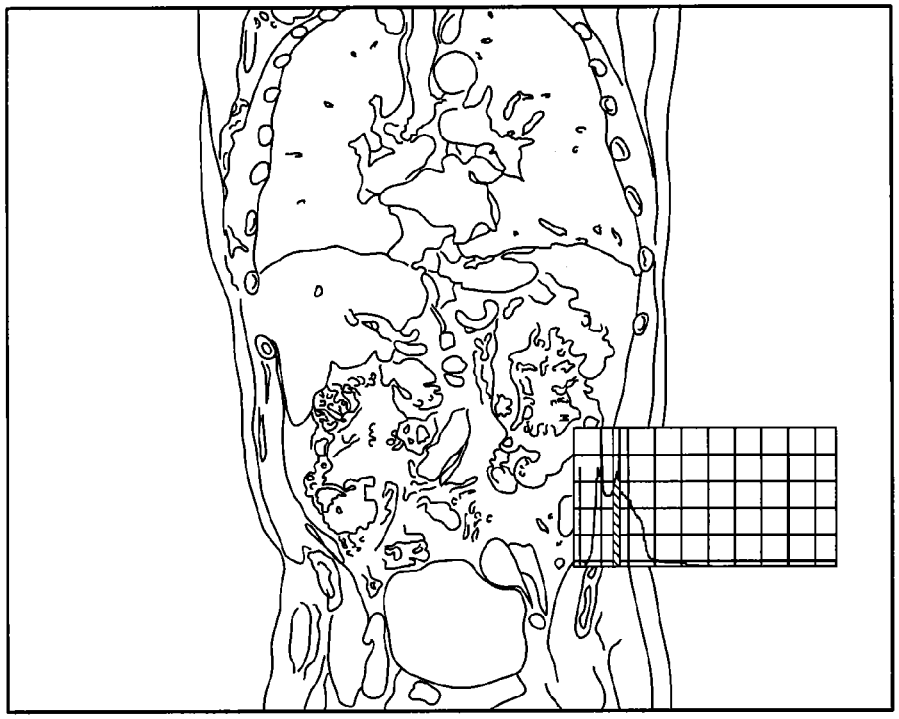
FIG. 6 is a multi-planar reformatting (MPR) image taken from a volume of CT data which is visualized with an abdomen preset, the figure including as an inset the histogram of the Image marked with the window level and window width of the abdomen preset.
Figure 7:
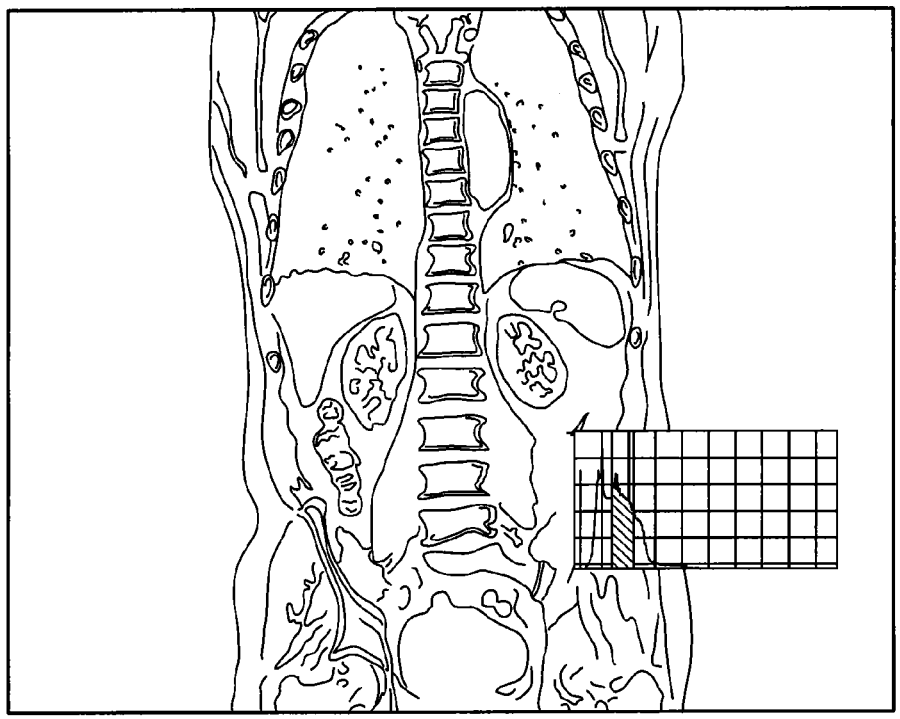
FIG. 7 is an MPR image of the same volume of CT data as FIG. 6 which is visualized with a bone preset, the figure including as an inset the histogram of the image marked with the window level and window width of the bone preset.
Figure 8:
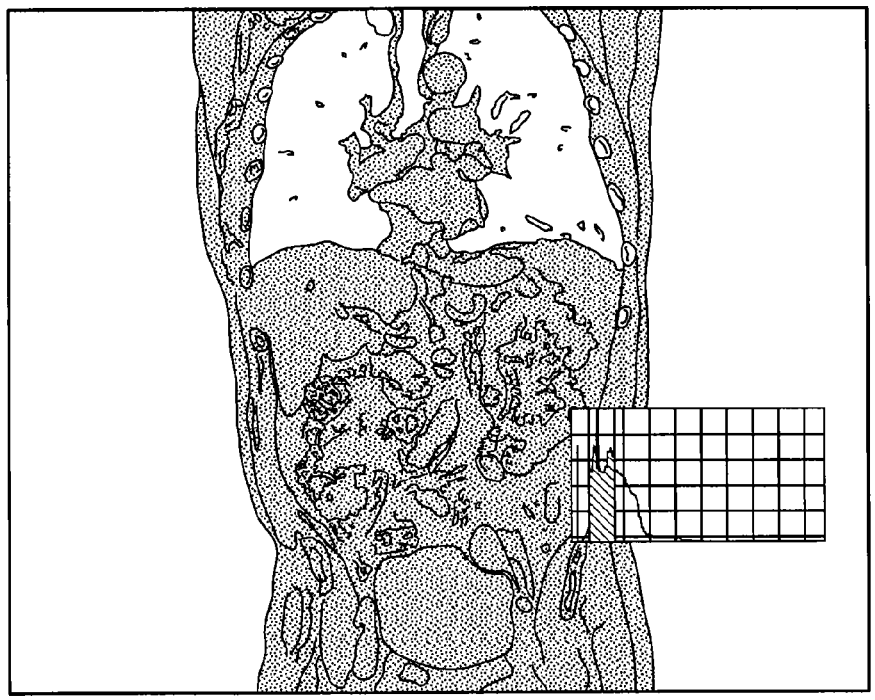
FIG. 8 is an MPR image of the same volume of CT data as FIG. 6 and FIG. 7 which is visualized with a lung preset, the figure including as an inset the histogram of the image marked with the window level and window width of the lung preset.

When the computer is running a visualization application and a patient study is loaded for view, the visualization application will typically prompt the user to choose from a list of presets in which the window width(s) and window level(s) have already been set to values which are known to be suitable for visualizing a particular part of anatomy, for example a lung study. The visualization application may also allow the user to manually adjust the window level and window width away from the values of the selected preset, and also create new presets ab initio. As the user navigates through the anatomy in a given study, they will often adjust the preset to better differentiate between the boundaries between the localized anatomical structures. When imaging a particular data set or part thereof, such as an area of interest in a 2D data set or a volume of interest in a 3D data set, the selected preset is usually illustrated alongside the image, e.g. as an inset, by showing its window level and width in a histogram graph, wherein the height of each bar of the histogram shows the number of voxels in that value range contained in the visualized data. Since the human body contains a large amount of different tissue types and any one of a considerable number of contrast agents may have been introduced to provide image contrast, the list of available presets within a visualization application can be large and will tend to become ever larger as the vendor and users add more and more specialist presets. By way of example, the following is a list of some common X-ray presets which could be used for visualization of 2D X-rays or for MPR views of 3D CT data:

1) Abdomen
2) Calcium
3) Lung
4) Abdominal Angio
5) Fat
6) Mediastinum
7) Bone (Hard)
8) Liver
9) Thoracic Angio
10) Bone (Soft)
11) Liver (Contrast)
12) Head FIGS. 6, 7 and 8 show three different presets applied to the same underlying image data, which may be 2D X-ray data or MPR data, in order to change the presentation of the image. As well as the image, each figure shows as an inset a histogram of the underlying data and how the window level and window width values relate to these data.

FIG. 6 is an MPR view of a slab taken from a volume of CT data which is visualized with an abdomen preset. The figure includes as an inset a histogram of the image marked with the window level and window width of the abdomen preset. As is apparent in this MPR image, it is possible to distinguish between a number of the anatomical structures within the abdomen. Although these have relatively close Hounsfield Unit data values, the associated window width and window level are fairly narrow and focused (about 400 HU, positioned at approximately 50 HU). The resulting image therefore can apply 256 shades of grey across 400 discrete data values. Data values which are less than −150 HU are represented in the image in black, whereas values greater than 250 HU are represented as white.

FIG. 7 is an MPR image of the same slab from the same volume of CT data as FIG. 6, but which is visualized with a bone preset, rather than an abdomen preset. The figure includes as an inset a histogram of the image marked with the window level and window width of the bone preset. Bone is known to have high values of Hounsfield Unit and therefore a suitable preset needs to set window width (W) and window level (L) to relatively high values such as, in this example, W: 1200, L: 350. The more dense the particular bone is, the whiter it will appear in the image. The surrounding anatomical structures are visible, but mostly appear as fairly uniformly light gray. Generally, it Is not possible to distinguish between these other non-bone structures, since the range of grayscale values associated with them is small.

FIG. 8 is an MPR image of the same slab from the same volume of CT data as FIG. 6 and FIG. 7, but which is visualized with a lung preset. The figure includes as an inset a histogram of the image marked with the window level and window width of the lung preset. Since a lung mostly contains air, it is important that the image shows a contrast between air and small internal vessels of the lung. As can be seen from this image, the lungs and associated vessels are easily distinguished; whereas the features in the various other anatomical regions mostly appear white and are less easily distinguished from one another.

The approach taken in certain embodiments of the invention is for the visualization application to be configured so it does not present the user with all available presets for selection, but instead makes an intelligent selection from the available presets based on user input on the displayed image of a location of interest. For example, if the user points and clicks with a mouse to a location on the image which is of interest, the visualization application makes an assessment of the properties of that location, and then presents the user only with those presets for selection which are consistent with those properties. Although a location based approach of this kind will reduce the otherwise long list of presets presented to the user for selection to a shorter list, there are further optimizations that can be accomplished to improve the efficiency. These include the following:

Metadata available from the DICOM header
Known anatomy contained within the data
Image analysis results, such as segmented objects In order to filter presets presented to the user based on header information and/or study-specific information manually input by a user or obtained automatically by segmentation, the preset library needs to associate relevant additional Information with each preset. An example table of CT presets is given below in which each preset is stored in the library with its modality (e.g. CT, MR, PET etc), anatomy (all, head, mediastinum, abdomen, leg/arm etc), whether a contrast agent is applied or not (yes/no) and whether the preset is the default preset for that modality.

| Preset Name | Modality | Suitable Anatomy | Contrast Agent | Default Preset |
|---|---|---|---|---|
| Abdomen | CT | Abdomen | no | |
| Abdominal Angio | CT | Abdomen | no | |
| Angio | CT | all | yes | |
| Bone (Hard) | CT | all | no | |
| Bone (Soft) | CT | all | no | yes |
| Calcium | CT | all | no | |
| Fat | CT | all | no | |
| Liver | CT | Abdomen | no | |
| Liver (Contrast) | CT | Abdomen | yes | |
| Lung | CT | Abdomen | no | |
| Mediastinum | CT | Abdomen | no | |
| Thoracic Angio | CT | Abdomen | yes | |
| Head | CT | Head | no | |

These data presented above as a table could be stored in a look up table. Alternatively, these data may be stored in a database.

The example lists of presets contain three which are only appropriate for data which are captured while the patient has been given Contrast (Anglo, Thoracic Angio and Liver (Contrast)). Contrast will appear in a CT scan similar to higher density anatomy. This is useful for visualizing small structures, such as vessels, etc. However, it's often the case that the clinical application and/or the user is aware that the data contains Contrast (or not). This information may be stored in the DICOM header as metadata. If this is the case, this header information can be used to include (or remove) presets specific to contrast agents from the filtered list presented to the user. Alternatively, the GUI may provide the user with a facility to specify whether to assume a contrast agent has been used or not.

It is possible that the DICOM information associated with the data also contains information about the anatomy that it contains. This would mean that the application could automatically filter out any presets which are not appropriate for the anatomy based on reference to the header information. For example, if the user is visualizing a scan of a patient's abdomen, any head-specific presets could be removed. Alternatively, the GUI may provide the user with a facility to specify the anatomy manually and exclusion of presets would occur based on the user's manual input, e.g. that the loaded patent data set was a head study.

Figure 9:
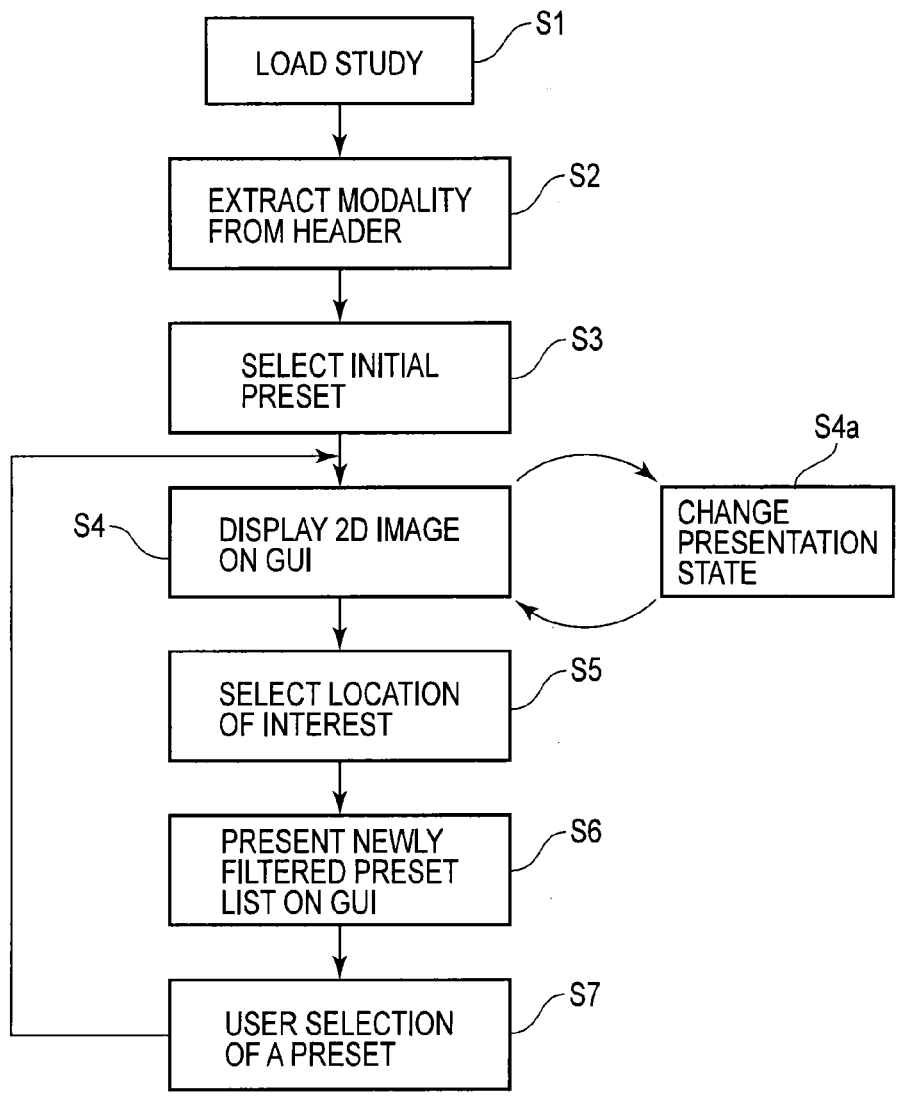
FIG. 9 is a flow diagram of a process for presenting intelligently filtered lists of presets to a user on a GUI.

FIG. 9 shows the process flow of an example selection process which is now described in more detail.

In Step S1, a study selected by a user is loaded. A study will take the form of a single DICOM file or a group of DICOM files.

In Step S2, header information is searched to extract the modality of the study. Thereafter in the process, only presets having the modality of the study are considered. For example, in a CT study, MR presets will be excluded as well as all presets from other modalities.

In Step S3, an initial preset is selected automatically by the process without user input. The initial preset may be a default preset for the modality or a default preset obtained from the diagnostic device used to acquire the volume data set. Optionally, if a preset with specific visualization parameter settings is stored in the header information, for example as a part of the operational state data stored from a previous session, then this preset can be selected, provided the preset exists in the library. A variation of this approach would be if the name of a preset was stored in the header information without further information, in which case if there was a text match of name in the preset library, the matching preset could be selected as the initial preset. Another option would be that the initial preset is a default specific to the user. Yet another option would be to choose a preset that covered the whole actual or potential data range, for example with linear sensitivity over that range. Alternatively, the process may prompt the user to define the initial preset from the full list of presets for that modality.

In Step S4, a 2D image is displayed in an initial representation with the initial preset on a graphical user interface (GUI) to the user. Step S4a is shown to indicate the users freedom to change the presentation state of the image. By changing the presentation state, we mean adjusting the image by controls such as pan, tilt and zoom as well as sculpting, thereby to change which subset of the patient data set is shown in the 2D image presented on the GUI. For example, the current view may be restricted to the head, whereas the volume data set contains a whole body image. Standard manipulations include pan, tilt, zoom in, zoom out and in the case of rendered views sculpt. Selection of a particular organ may also be considered to be a manipulation.

In Step S5, the user inputs a location of interest by pointing on the 2D image, the location being indicative of a region that is of interest to the user. This prompts the application to determine relevant properties of the image elements in the region of interest and then to recalculate which presets are potentially suitable on that basis. As well as applying information derived from image elements at or near the selected location, such as the signal value of the selected pixel or pixels, the recalculation may optionally refer to metadata available to the application, such metadata either having been manually input by the user during the session or by extracting the metadata from header information associated with the image data, which is relevant to how the user wishes to visualize the study. In addition, the recalculation may optionally have regard to the subset of the image data being shown on the GUI which may have changed since the last refresh as a result of the user changing the presentation state in Step S4a. For example, if the user has sculpted away certain tissue types, then presets specific to the removed tissue types would be deemed not suitable, whereas if the user has manipulated the presentation state of the image to select a particular organ, then presets specific to that organ will be deemed suitable.

Figure 10A:
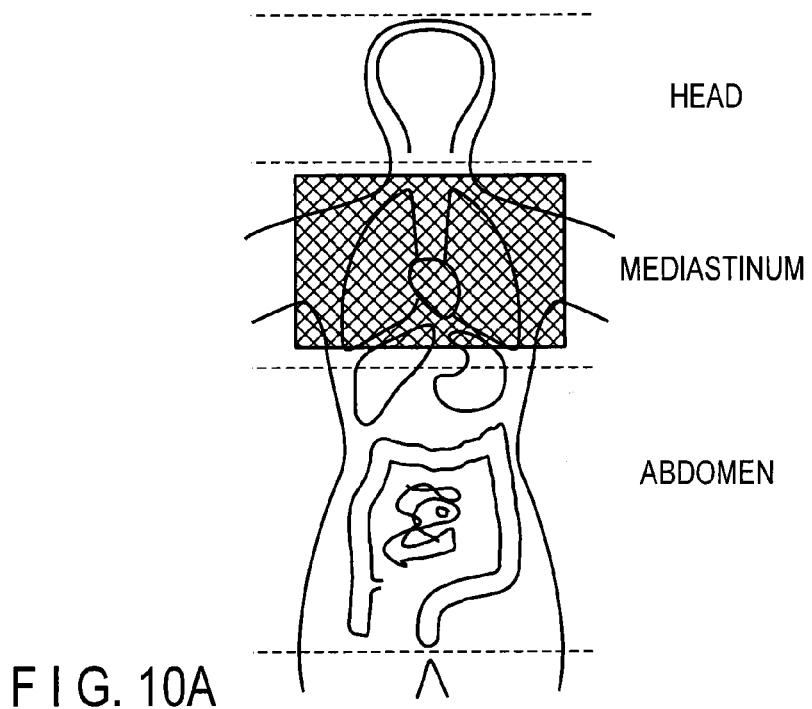
FIG. 10a is a schematic outline of a human body with some of the principal organs shown as well as a cross-hatched rectangle which represents a users current field of view on a display.
Figure 10B:
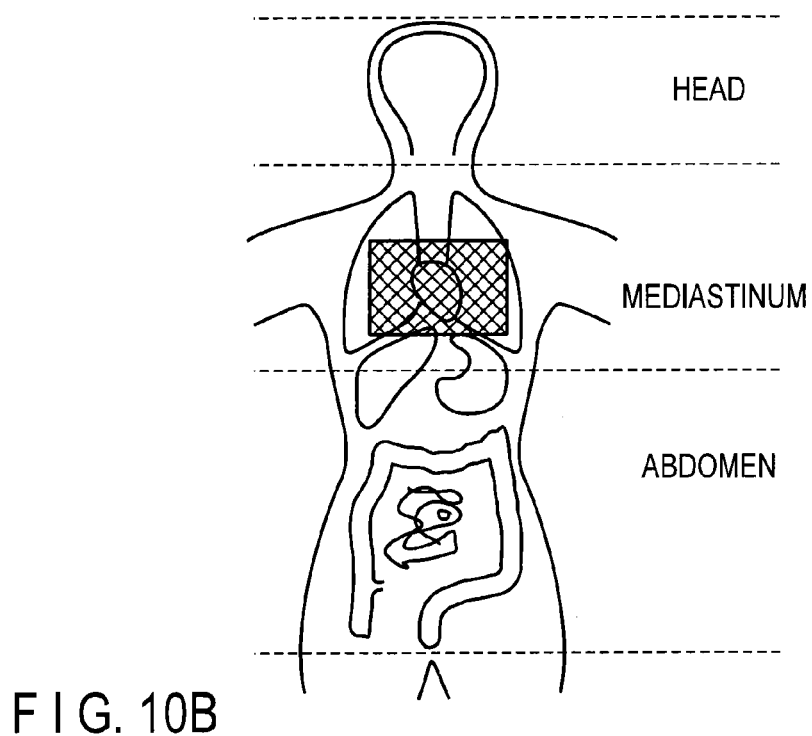

FIG. 10a and FIG. 10b are used to illustrate an example image manipulation. FIG. 10a is a schematic outline of a human body with some of the principal organs shown as well as a cross-hatched rectangle which represents a users current field of view on a display which is of substantially the entire mediastinum including the whole region of the lungs and heart. The user may then change the presentation state by zooming in on the heart as shown schematically in FIG. 10b, which is the same as FIG. 10a except that the field of view has been zoomed in. The user may change the presentation state of the image displayed on the GUI repeatedly as indicated by the loop between Steps S4 and S5 in FIG. 9. The manipulation may not be a pure zoom, it may include a pan for example. The user may also perform a sculpt to remove the lungs and/or select the heart as the object of interest.

In Step S6, the presentation of suitable presets is refreshed by a newly filtered list being presented on the GUI. The filtering may be in response to changes caused in Step S5 and also in some cases by changes in presentation state in Step S4a which may lead to some anatomy appearing in or disappearing from the displayed portion of the image, for example as the image is panned or zoomed. It is envisaged that the refresh is triggered by a location input by the user which effectively prompts the system to perform the refresh. A refresh of the preset filtering may also be triggerable manually by the user, for example with a separate button on the GUI provided for that purpose. As well as or instead of filtering, sorting may be applied so that the presets deemed to be of most interest are sorted to the top of a long list which might also include presets deemed to be unsuitable lower down the order.

In Step S7, there is user selection of a preset from the list of presets currently displayed in the dropdown list on the GUI. This user preset selection prompts re-rendering of the image using the newly selected preset by returning the process flow to Step S4. After user selection of a preset in Step S7, the process flow then returns to Step S4.

The GUI may also provide the user with the option of saving the currently selected preset in the header information so that this preset is available for use as the initial, default preset when the study is loaded In the future. Use of the stored default preset when re-loading the study may be activated conditional on the same user carrying out the re-loading, or may be generic to all users, or may be generic to any user without a user-specific default preset already stored in the header Information of the DICOM file(s) for the study.

It will be appreciated that other schemes for allowing a user to identify pixels or voxels can also be used. For example, rather than "clicking" on an individual pixel in one of the section views, a range of pixels could be identified by a user "clicking" twice to identify opposite corners of a rectangle, or a center and circumference point of a circle, or by defining a shape in some other way. For example, a shape may be identified in a touch screen through a gesture, such as a multitouch gesture using thumb and forefinger, as is known in the art. Pixels, or voxels corresponding to pixels in a 2D representation of a 3D data set, within the perimeter of the shape may then all be deemed to have been identified.

In the method, the list of presets is filtered in response to a location-specific user input, such as a mouse click or touch of a touch screen. This approach removes the requirement on the user to navigate through a long list of presets, many of which will be irrelevant, by instead providing the user with an intelligently selected subset of presets which have been filtered according to interactive user input on a display of an image of the currently loaded study.

Some specific examples showing how filtering affects the dropdown list of presets for an example image are now described.

FIGS. 11a to 11g are different screen shots from a GUI of the same image data set, each screen shot being of a horizontal section of a patient's abdomen where the underlying data is in each case the same. The underlying data is a patient data set of conventional 2D X-ray data obtained from a CT scan. Each screen shot also shows the dropdown list of presets which appears, e.g. following the user "clicking" at the indicated cursor location to communicate to the visualization application the users location of interest.

FIG. 11a illustrates the GUI with a dropdown menu of the full list. Presenting such a long list to the user is not ideal, since the time navigating through large menus (and submenus) increases the overall case reading time for the user. This example list also does not include potential custom presets which would result in a longer list.

A first mechanism to filter the presets presented to the user for selection is to identify the ranges of voxel values which the user may be visualizing and the presets which are most appropriate for these. For CT scans, the Hounsfield Scale (HU) ranges from air (−1000) to dense structures such as bone (1000) with softer tissues types having intermediate values. The following table gives examples of these ranges along with example appropriate presets.

| Air (<−100) | Soft Tissues (−100 to 100) | Dense Structures (>100) |
| --- | --- | --- |
| Lung | Abdomen | Angio |
| Mediastinum | Abdominal Angio | Bone (Hard) |
| Thoracic Angio | Liver | Bone (Soft) |
| | Liver (Contrast) | Calcium |
| | Mediastinum | |
| | Head | |
| | Fat | |

By utilizing these scales and the location where the user gestured, it is possible to narrow down, i.e. filter, the list of possible presets to filter out those presets which are not clinically useful for the location of interest in the imaged volume.

FIG. 11b shows an example GUI when the user clicks on a portion of the 2D representation signifying air, and the user is then presented with a filtered list of CT presets which include visualization of the range of HUs relating to air, i.e. <−100.

Figure 11C:
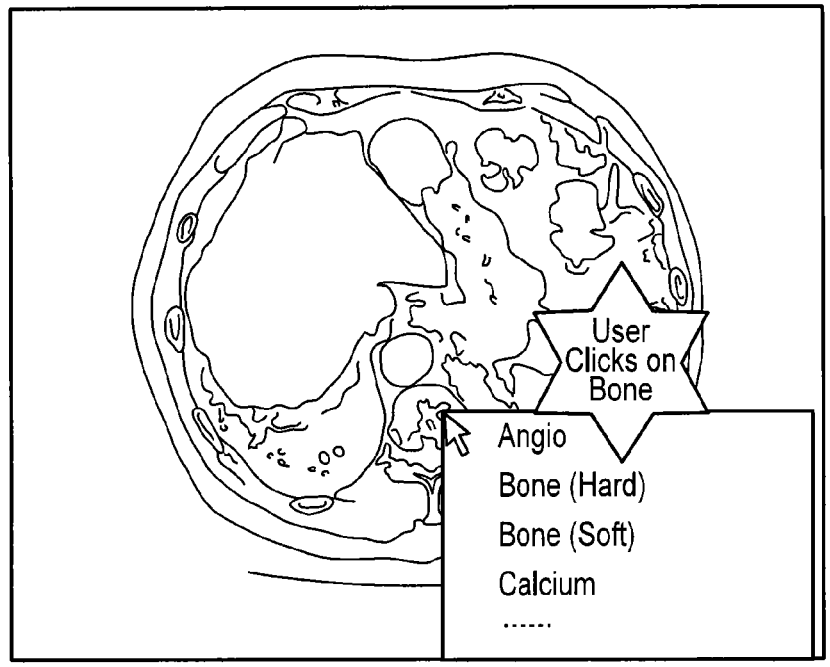

FIG. 11c shows an example GUI when the user clicks on a portion of the 2D representation signifying bone, and the user is then presented with a filtered list of CT presets which include visualization of the range of HUs relating to bone, i.e. >100.

Figure 11D:
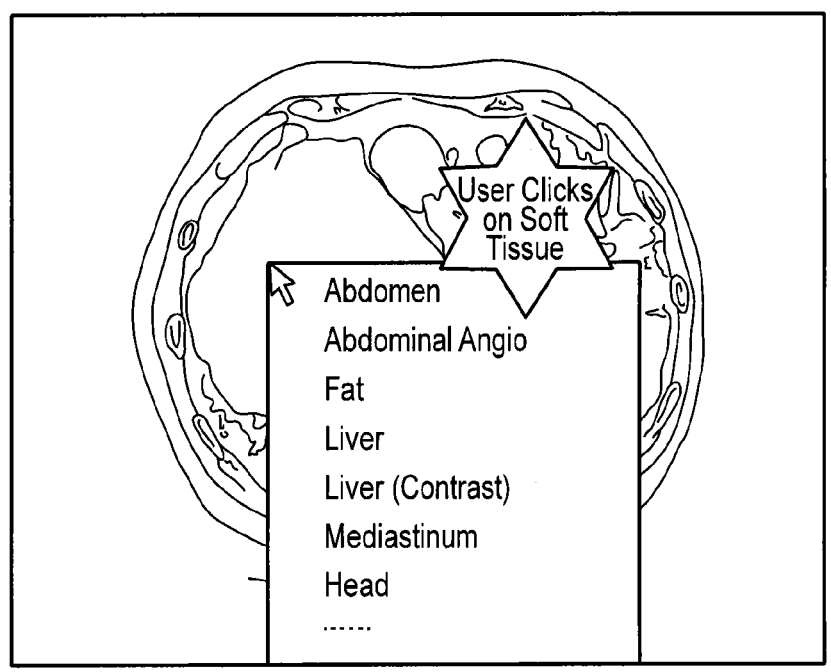

FIG. 11d shows an example GUI when the user clicks on a portion of the 2D representation signifying soft tissue, and the user is then presented with a filtered list of CT presets which include visualization of the range of HUs relating to soft tissue, i.e. −100 to 100.

The filtering of suitable presets is achieved by sampling the underlying voxel value in HU of the voxel which the pixel represents and identifying in which preset range it lies. Once this has been achieved, the list of all presets suitable for that range of HUs is displayed. This filtered list is normally far less than the entire collection and may only consist of a single preset.

FIG. 11e shows a filtered evolution from the initial list of FIG. 11a in which the filtering has removed contrast-specific presets based on header information or user input specifying that the study is a non-contrast study, and also has removed presets not within the HU range of the high density structure selected by the user.

FIG. 11f shows an example GUI in which only abdomen-suitable presets are listed together with filtering based on the selected location of Interest, which is soft tissue, and filtering based on header information or user input that the image has no contrast agent. The list of presets in FIG. 11f is thus an evolution from the list of FIG. 11*d* with the "Head" preset removed based on the anatomy and the "Abdominal Anglo" and "Liver (Contrast)" presets removed based on there being no contrast agent.

A further refinement of the method is to include segmentation so as to translate the user's input regarding the location of interest to an anatomical feature. Automatic segmentation algorithms, allow anatomical structures and their bounds to be identified within the volume data set, such as bone, vessels, lung, liver, heart, brain etc.

Segmentation data may be used in two ways. First, the voxel values, such as HUs, included to make the filtering of the presets can be taken from the whole of the segmented feature, e.g. the whole of the liver if the user identifies a point in the liver as the location of interest. Second, the presets can be filtered based on their anatomical relevance. For example, if the user clicks on what is known from segmentation to be a location in the heart, then liver-specific presets can be filtered out, even though both presets may visualize the same or overlapping ranges of opacity. As mentioned above, the segmentation could be pre-existing or calculated "on the fly" as part of the preset selection process in response to user input of location(s) of interest and optionally also locations not of interest. Segmentation on the fly could be initiated conditional on quantity and/or type of user input of locations. For example, selections of locations of interest, segmentation could be initiated only after a threshold number of positive selections has been made, e.g. 4, 5, 6, 7, 8, 9 or 10. Another example is where segmentation on the fly is only initiated if there is a negative selection, i.e. selection of a location not of interest, as well as a positive selection, or a threshold number of both positive and negative selections, e.g. 2, 3, 4, 5, 6, 7, 8, 9 or 10 positive selections and 2, 3, 4, 5, 6, 7, 8, 9 or 10 negative selections.

Figure 11G:
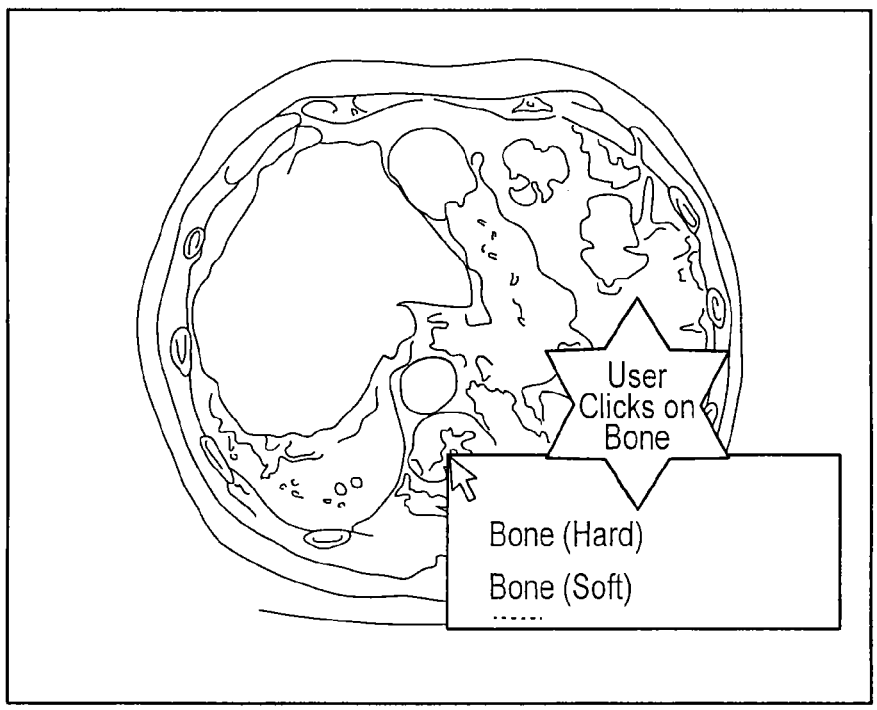

FIG. 11*g* shows an example GUI when the user clicks on a portion of the 2D representation signifying bone. The segmentation information "knows" that the clicked location is part of a bone, so the user is only presented with bone-specific CT presets.

Another illustrative example is now given based on reconstructed M PR views instead of views of 2D X-ray data as in the previous example. In actual fact, the implementation of the visualization application could be the same for both MPR and conventional 2D, since in both cases the displayed Image is made up as a collection of pixels, and in the MPR case the underlying voxel data value (in HU) for each such pixel can be determined.

Figure 12A:
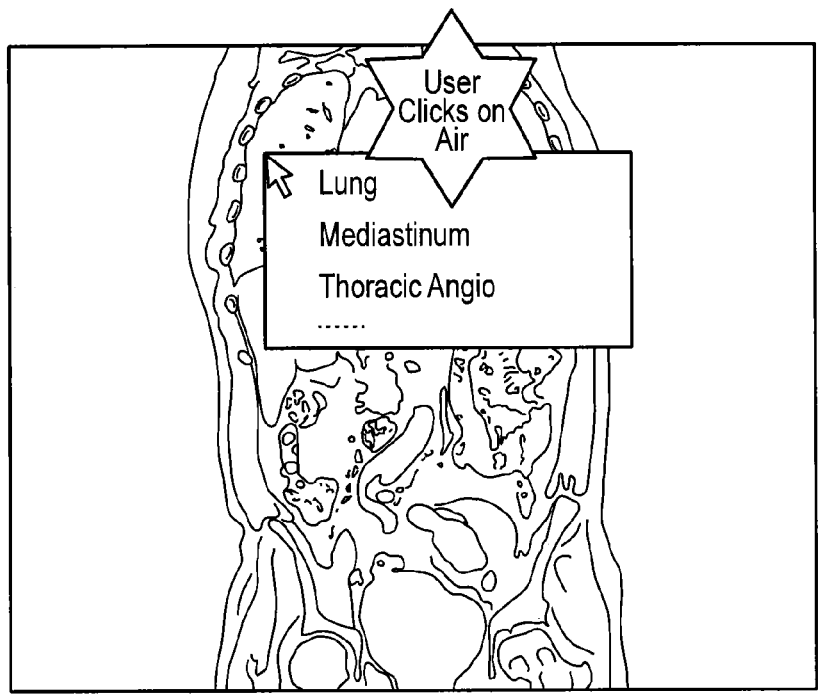
FIG. 12a is a first example screen shot from a GUI presenting a 2D MPR image which is a vertical (or transverse) section of a patient's abdomen obtained from a CT volume data set of the abdomen region together with a dropdown list of presets available for user selection when the user "clicks" on, i.e. selects, a portion of the image containing air.

FIG. 12*a* is a first example screen shot from a GUI presenting a 2D MPR image which is a vertical (or transverse) section of a patient's abdomen obtained from a CT volume data set of the abdomen region together with a dropdown list of presets available for user selection when the user "clicks" on, i.e. selects, a portion of the image containing air.

Figure 12B:
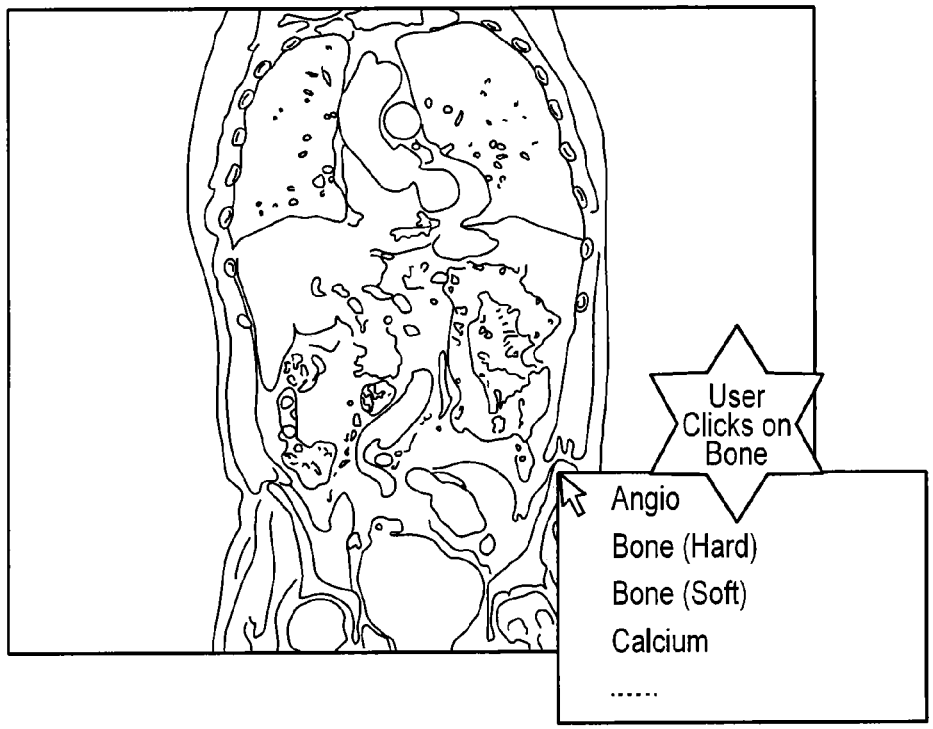
FIG. 12b corresponds to FIG. 12a, but shows the dropdown list of presets available for user selection when the user "clicks" on, i.e. selects, a portion of the image containing bone.

FIG. 12*b* corresponds to FIG. 12*a*, but shows the dropdown list of presets available for user selection when the user "clicks" on, i.e. selects, a portion of the image containing bone.

The MPR view behaves in exactly the same way as that of the 2D view of the previous example. The user indicates that they are interested in air or bone, for which a filtered list of suitable presets is displayed. When using a non-slabbed MPR view, the point which the user has indicated as being of special interest (e.g. by mouse click) can straightforwardly be translated back to the original underlying signal value. However, an MPR view is often configured to sample a number of voxels from the data in order to render the final image. For example, if the original image slices were 1 mm apart from each other, the user could configure a "Slab" of 5 mm, which would result in data from up to 5 images being used to determine the final rendered value. However, the mechanism in which these different data values are combined to reach a final value can also be configurable based upon the "Projection Mode". There are commonly three different types of Projection Mode used by MPR Slabs:

AveIP (Average intensity Projection)—The voxel data values are averaged to produce their collective value MIP (Maximum Intensity Projection)—The maximum voxel data value is used.

MinIP (Minimum Intensity Projection)—The minimum voxel data value is used.

This means that when sampling a point from a slabbed MPR view, it is important to use the collective value as computed with the Projection Mode. This sampled value can then be used to determine which collection of Window Level Presets would be best to visualize that particular anatomical region.

As well as filtering the presets in order only to present to the user an intelligently reduced list of potentially suitable presets, the method may be further refined to apply logic to sorting or ordering the list presented to the user, with those presets deemed to be most suitable listed first.

Sorting may be based on user profiling, for example on the basis of a log of how often the user has used the presets in the past, for example usage in a limited time period of the recent past. The sorting may be done based on a generic log of all the user's activities, or a log specific to the study currently loaded. User profiling may also be used to integrate user-specific custom presets in the overall presentation of potentially suitable presets.

It will be understood that some presets use a grayscale, as in the examples described in this document, whereas other presets use color. For example, the signal values of pixels or voxels within a region of interest (and hence the corresponding portions in the projected image) can be shown as different colors. For example, pixels or voxels associated with a blood vessel network can be shaded yellow, those of soft tissue are allocated shades of transparent red and those of bone can be allocated shades of cream. An example figure is not included to avoid use of color in the drawings.

In some visualization applications, presets may be required to satisfy further conditions before they are accepted for defining grayscale or color range boundaries (or other visualization parameters). For example, in applications where bone visualization within a CT data set is of prime interest, visualization thresholds should not be defined between those signal values representing soft tissue and blood vessels since both of these should be made transparent in the displayed image. Instead, less significant but more appropriate thresholds within the range of signal values representing bone may be preferred.

Moreover, while the above preset examples concentrate on visualization thresholds which are used to define grayscale (or color) boundaries, it will be appreciated that visualization thresholds are equally suitable for defining boundaries for visualization parameters other than grayscale or color, such as opacity or texture, that are relevant for rendering. Furthermore, it is often clinically useful for the placement of boundaries in an opacity mapping to be positioned at the same signal values as the boundaries in a color mapping. Other visualization parameters include rate of change of color with signal value, rate of change of opacity with signal value, and segmentation information.

Embodiments of the invention may include incorporating the methods and associated computer programs described herein as a component in a volume rendering application.

A computer program product bearing machine readable instructions for carrying out the method is disclosed.

A computer loaded with and operable to execute machine readable instructions for carrying out the method is disclosed.

A computer program product is disclosed. Examples of a computer program product bearing machine readable instructions for carrying out the method described above are the mass storage device HDD 30 of FIG. 3, the ROM 26 of FIG. 3, the RAM 28 of FIG. 3 and the system memory 46 of FIG. 4, and the servers 13, 18 of FIG. 1. Other forms of computer program product include a spinning disk based storage device such as a CD or DVD, or a USB flash memory device.

Examples of a computer loaded with and operable to execute machine readable instructions for carrying out the method described above are the computer of FIG. 3, the computer of FIG. 4, and individual elements, e.g. terminals or collective multiple elements of the computer network system shown in FIG. 1, e.g. one of the servers 13, 18 in combination with one or more of the terminals or computers provided with the medical imaging devices.

Examples of a computer program product bearing machine readable instructions for carrying out the method described above are the mass storage device HDD 30 of FIG. 3, the ROM 26 of FIG. 3, the RAM 28 of FIG. 3 and the system memory 46 of FIG. 4, and the servers 13, 18 of FIG. 1. Other forms of computer program product include a spinning disk based storage device such as a CD or DVD, or a USB flash memory device.

While the method has been described with reference to X-ray image data sets collected by conventional X-ray devices or CT scanners, it is more generally applicable to imaging of other 2D and 3D data sets and also so-called 4D data sets, i.e. time sequences of volume image data sets. For example, the method may be applied to other imaging types used in the medical field, referred to as modalities. In particular, the methods described herein may be applied to MR images and PET images as well as to images of merged data sets from two modalities such as CT and PET.

While certain embodiments have been described, these embodiments have been presented by way of example only, and are not intended to limit the scope of the inventions. Indeed, the novel methods, computers and computer program products and devices described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A computer-automated image visualization method for displaying images from an image data set comprising a plurality of image elements, each image element having an associated image value, the method comprising:
   a) providing a visualization application with a library of presets, each preset defining a mapping between image values and their representation in a graphical user interface;
   b) loading an image data set from a data file containing the image data set;
   c) displaying an initial representation of the loaded image data set on a graphical user interface;
   d) receiving user input from a location in the representation to indicate a region of interest in the image data set;
   e) determining properties of image elements in the region of interest;
   f) making a list of potentially suitable presets from the library of presets based on the determined properties of the region of interest; and
   g) presenting the potentially suitable presets to the user for selection;
       wherein the image data set is a volume data set having voxels as its image elements, each voxel has an associated voxel value as its associated image value, and the property of voxels used for the determination comprises statistical fluctuation in voxel value in said group of voxels.

2. The method of claim 1 further comprising: making the list based also on header information stored in the data file.

3. The method of claim 2, wherein the header information used in making the list is selected from the group including:
   a) modality information;
   b) contrast agent information;
   c) anatomical information defining the imaged body portion;
   d) medical information specific to the diagnostic purpose of the image data set;
   e) medical information specific to the clinical position of the user.

4. The method of claim 1 further comprising:
   making the list based also on segmentation data providing anatomical information about the region of interest.

5. The method of claim 1, wherein the list comprises a subset of the presets contained in the library.

6. The method of claim 1, wherein the list is sorted according to potential suitability.

7. The method of claim 6, wherein presets determined to be most suitable are listed first.

8. The method of claim 1, wherein the list comprises a subset of the presets contained in the library sorted according to potential suitability with presets determined to be most suitable listed first.

9. The method of claim 1, wherein the potentially suitable presets are presented on the graphical user interface adjacent to the location where the user input is received.

10. The method of claim 1 further comprising:
    storing the list of potentially suitable presets in header information of the data file.

11. The method of claim 1 further comprising:
    receiving the user selection from among the potentially suitable presets; and
    displaying a representation of the volume data set using the selected preset.

12. The method of claim 1, wherein, if the list consists solely of one potentially suitable preset, the method proceeds directly to display a representation of the image data set using that preset instead of step g).

13. The method of claim 1, further comprising:
    storing the user selected preset in header information of the data file.

14. The method of claim 1, wherein the region of interest includes a group of voxels defined by proximity to a point identified by the user input.

15. The method of claim 1, wherein the region of interest includes a group of voxels defined by a segmentation seeded from a point identified by the user input.

16. A non-transitory computer program product bearing machine readable instructions for carrying out the method of claim 1.

17. A computer system loaded with and operable to execute machine readable instructions for carrying out a computer-automated image visualization method for displaying images from an image data set comprising a plurality of image elements, each image element having an associated image value, the computer system comprising:

- a first memory unit storing a data file containing an image data set;
- a second memory unit storing a visualization application with a library of presets, each preset defining a mapping between image values and their representation in a graphical user interface;
- an image processing unit operable to load an image data set from the data file;
- a display unit operable to display an initial representation of the loaded image data set on a graphical user interface;
- a user input device operable to receive user input from a location in the representation to indicate a region of interest in the image data set;

the image processing unit being further operable to:
  i. determine properties of image elements in the region of interest;
  ii. make a list of potentially suitable presets from the library of presets based on the determined properties of the region of interest; and
  iii. present the potentially suitable presets to the user for selection on the display unit;

wherein the image data set is a volume data set having voxels as its image elements, each voxel has an associated voxel value as its associated image value, and the property of voxels used for the determination comprises statistical fluctuation in voxel value in said group of voxels.

18. An image acquisition device loaded with and operable to execute machine readable instructions for carrying out the method of claim 1.

* * * * *